United States Patent [19]

Paulson

[11] Patent Number: 5,505,019
[45] Date of Patent: Apr. 9, 1996

[54] PESTICIDE APPLICATOR AND COMPOSITION

[76] Inventor: Peter O. Paulson, 320 Pumphill Gardens S.W., Calgary, Alberta, T2V 4M7, Canada

[21] Appl. No.: 230,710

[22] Filed: Apr. 21, 1994

[51] Int. Cl.$^6$ ................................................ A01M 21/04
[52] U.S. Cl. ........................ 47/1.5; 106/270; 239/60
[58] Field of Search ........................ 239/60; 47/1.5; 106/270, 272

[56] References Cited

U.S. PATENT DOCUMENTS

| | | | |
|---|---|---|---|
| 2,720,013 | 10/1955 | Clarke | 239/60 |
| 3,096,534 | 7/1963 | Jones | 47/1.5 |
| 3,844,428 | 10/1974 | Davis | 239/60 |
| 3,925,927 | 12/1975 | Linton | 47/1.5 |
| 4,088,473 | 5/1978 | Linton | 71/92 |
| 4,278,360 | 7/1981 | Lorscheid | 47/1.5 |
| 4,716,677 | 1/1988 | Moore | 47/1.5 |
| 4,793,850 | 12/1988 | Koester | 71/79 |
| 4,882,874 | 11/1989 | Paulson | 47/1.5 |
| 5,074,902 | 12/1991 | Connick | 71/79 |

Primary Examiner—Henry E. Raduazo
Attorney, Agent, or Firm—Bennett Jones Verchere

[57] ABSTRACT

A pesticide applicator has a mounting surface onto which is bonded a solid pesticide composition. The bonding is provided by a cellulosic sheet disposed between the pesticide and the mounting surface avoiding the requirement for surface knurling or fasteners such as are found in previous solid pesticide applicators. A solid pesticide composition is also disclosed comprising a solid carrier, a pesticide and an amount of flour to promote the dispersion of the pesticide into the wax. Previously known chemical surfactants are not required.

8 Claims, 2 Drawing Sheets

PESTICIDE APPLICATOR AND COMPOSITION

FIELD OF THE INVENTION

The present invention is directed to a pesticide applicator and composition. More particularly, the present invention is directed to an applicator for solid pesticides and a solid pesticide composition.

BACKGROUND OF THE INVENTION

Applicators are known for spot application of pesticides to plants. However, many spot applicators are for the application of liquid pesticides and require complicated valve systems to control the flow of the liquid.

Recently, there has been a desire to move away from liquid pesticides for spot applications and instead to use solid forms of pesticide. Such pesticides are solid at ambient temperatures and allow the application of pesticide directly to the plant, in a controlled amount, while reducing unwanted spillage onto surrounding foliage or soil.

An applicator for solid pesticide composition is taught in U.S. Pat. No. 4,882,874 issued Nov. 28, 1989. The disclosed applicator retains the block of pesticide in a paper sleeve and requires that knurls or indents be formed in the sleeve, or fasteners, such as staples, be inserted through the sleeve to engage the block and maintain the block in the sleeve. In use, this form of attachment requires that the applicator be discarded or reloaded once the block has been reduced to the level of the attachment. Thus, much of the pesticide block is wasted. In addition, the mechanical arrangement whereby the pesticide is advanced along the sleeve of the applicator has been found to fail in some instances. An applicator is required which overcomes these drawbacks.

Solid pesticide compositions are also known. Because of the hydrophobic nature of common solid carrier materials, such as wax, and the hydrophillic nature of many commonly employed pesticides, such as amine herbicide formulations, problems arise in the preparation of the solid pesticide. Since the two phases are naturally immiscible, surfactants are required to allow the production of a solid form without stratification. However, the surfactants, such as fatty amides, may themselves create adverse side effects. In addition, the cost of the solid pesticide is increased by the addition of such surfactants.

SUMMARY OF THE INVENTION

An applicator for solid pesticide compositions has been invented and is described herein which does not require engagement of the pesticide block within the applicator by means of surface indentations, engaging protrusions or fasteners. In this way, the applicator presents no restriction to the use of the pesticide and the entirety of the block can be used before disposal or reloading of the applicator. The applicator is assembled by means of a novel wax to surface attachment involving the use of cellulosic material and microcrystalline wax.

Additionally, a solid pesticide formulation has been invented which does not require the use of chemical surfactants.

In a broad aspect of the present invention, there is provided a method for mounting a wax-based composition containing microcrystalline wax onto a surface of cellulosic material comprising:

providing a surface of cellulosic material;

heating the wax-based composition to a predetermined temperature which is at least sufficient to melt the wax-based composition;

bringing the cellulosic material into contact with the wax-based composition; and, allowing the wax-based composition to solidify in contact with the surface of cellulosic material, wherein the predetermined temperature of the wax-based composition is sufficient to raise the temperature of the cellulosic material to a level which is at least sufficient to melt the wax-based composition.

In another broad aspect of the present invention, there is provided a pesticide applicator comprising a mounting surface, a block of pesticide-containing solid carrier and an intermediate layer of cellulosic material for mounting the pesticide-containing solid carrier onto the mounting surface, wherein the block of pesticide-containing solid carrier contains microcrystalline wax.

In an alternative embodiment, there is provided a pesticide applicator comprising a mounting surface and a block of pesticide-containing solid carrier, wherein the applicator mounting surface is formed from cellulosic material and the pesticide-containing solid carrier contains microcrystalline wax and is fused directly to the mounting surface.

In an additional aspect of the present invention, there is provided a solid pesticide composition comprising a solid carrier, a pesticide and a plant product able to absorb liquid to form a gel.

DESCRIPTION OF THE INVENTION

The applicator of the present invention is for use with solid carrier composition such as a solid pesticide composition wherein the pesticide is contained in a block of solid carrier, such as wax. The applicator comprises a mounting surface for supporting the block of solid carrier. The block is maintained on the mounting surface by means of a bond formed between the solid carrier and a cellulosic material. The bonding occurs when the cellulosic material is brought into contact with molten carrier composition containing microcrystalline wax. The molten composition causes the temperature of the cellulosic material to be raised to allow the infiltration of the molten carrier material between the fibres of the cellulosic material. The carrier is then allowed to cool to form a solid pesticide carrier which is bound to the cellulosic material. To form an applicator, the cellulosic material is firmly attached by any suitable means to the mounting surface of the applicator, either before or after the bonding step. Alternatively, the mounting surface is, itself, formed from cellulosic material. This attachment method is useful with all solid carrier compositions which contain microcrystalline wax, such as wax-based compositions and pesticide-containing wax-based compositions.

The cellulosic material must be of a suitable fibre density to allow the binding of solid carrier while being able to bear the stresses which will be present from the weight of the attached solid carrier block and the stresses encountered during use. Preferably, the cellulosic material is paper or wood.

The cellulosic material, in the form of a thin sheet, can be attached to the mounting surface by various means such as by permanent adhesives or pressure sensitive adhesives. The preferred thickness of the sheet is 0.003" to 0.020".

Alternatively, the cellulosic material may be formed as a rigid plaque or card which is slotted or snapped into the mounting surface. In this embodiment, the mounting surface of the applicator is adapted to mate with the card such as by the provision of flanges to form a slot or by the provision of a corresponding snap arrangement. In this way, reusable applicators can be made which can be reloaded with a new pesticide block when the original block is expired.

Alternatively, the mounting surface can itself be formed from cellulosic material such as card board or wood which may extend up to attach to or form the remainder of the applicator. Preferably, the cellulosic material is rigid or maintained rigid by the mounting surface so as to prevent concentration of stress at the bond.

Where the cellulosic material is an intermediate layer, infiltration of the carrier through the cellulose may hinder later adhesive mounting of the cellulose to the mounting surface. Thus, it is preferred that the layer of cellulosic material be mounted on the mounting surface prior to binding with the carrier. This, of course, is not a concern where an adhesive is used which can bond to wax-impregnated cellulose or where the carrier is applied to the cellulose in such a way that the later application of adhesives to the cellulose will not be affected.

To enhance the usefulness of the applicator a capping means can be provided which protects the carrier block from damage or contamination. It is to be understood that a variety of capping arrangements are useful in the present invention. For example, the cap can be attached to the applicator by snap or threaded attachments. Alternatively, the cap may be designed to engage directly a portion of the pesticide block or cellulosic material.

Further an extendable handle can be provided on the applicator. The handle can either be formed integrally with the mounting surface or alternatively, be detachable from the mounting surface, to allow compact storage and packaging.

The solid pesticide composition of the present invention comprises a solid carrier, a pesticide and a sufficient quantity of a plant product able to absorb liquids to form a gel. The plant product acts to allow the dispersion of the pesticide into the wax and maintains the pesticide in suspension in the wax. Starch or flour derived from plant products are preferred for use in the pesticide composition. The composition comprises an effective amount of pesticide and flour in a solid carrier. Preferably, the composition comprises, by weight, 75–90% solid carrier, and 10–25% flour and pesticide in the amount of 0.5 to 5.0% by volume of the pesticide composition. Of course, the amount of flour added to the composition depends on the amount of pesticide required for the composition to have an effective pesticidal action.

These foregoing aspects of the invention, together with other aspects and advantages thereof, will be more apparent from the following description of the preferred embodiments thereof, taken in conjunction with the following drawings.

BRIEF DESCRIPTION OF THE DRAWINGS

For a better understanding of the present invention, reference may be made, by way of example, to the following diagrammatic drawings, in which.

DETAILED DESCRIPTION OF THE PREFERRED EMBODIMENTS

Figure 1A:
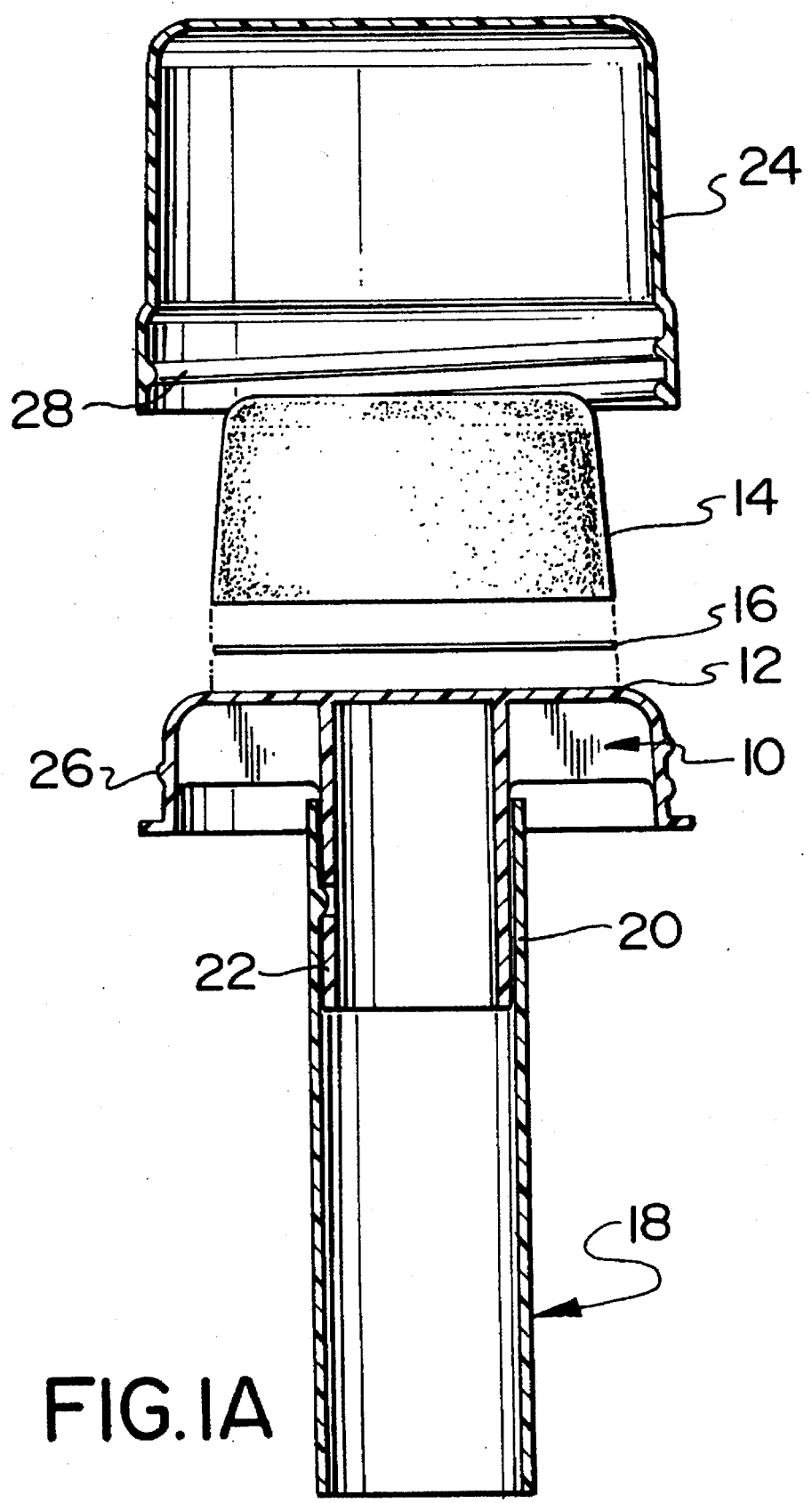
FIGS. 1A and 1B are sectional views through an applicator of the present invention in exploded and assembled form, respectively.
Figure 1B:
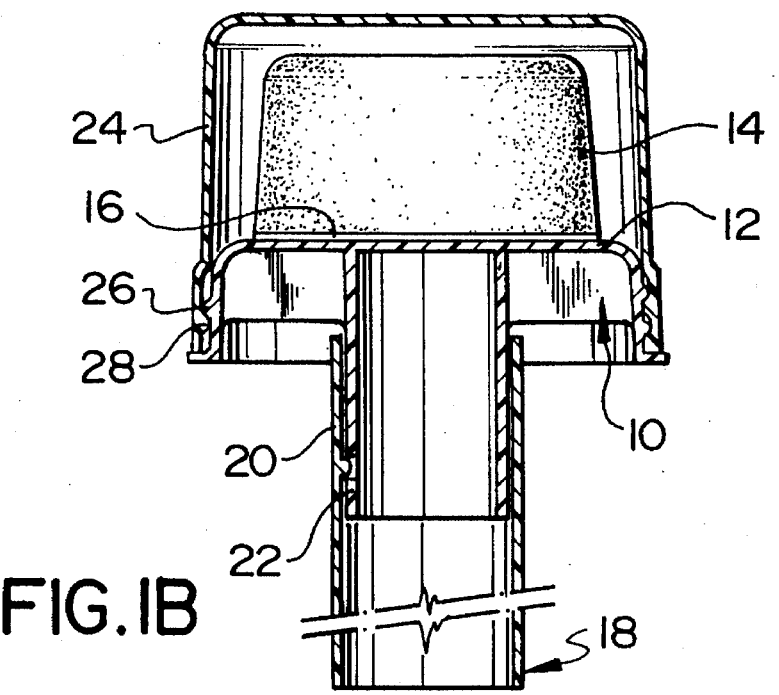

Referring to FIGS. 1A and 1B, the pesticide applicator of the present invention comprises a body 10 having a mounting surface 12 for supporting a pesticide-containing block of solid carrier material 14 containing microcrystalline wax. Block 14 is maintained on mounting surface 12 by means of an intermediate layer of cellulosic material 16, such as paper or wood, which is mounted onto the mounting surface and fused to the block.

Cellulosic layer 16 is mounted on mounting surface 12 by means of adhesives. Preferably, a cyanoacrylate adhesive is used. To enhance the mounting of the cellulosic material, the mounting surface is preferably substantially planar and the adhesive is applied over the entire surface which will be in contact between the mounting surface and the cellulosic material, to hold the cellulosic material rigidly against the mounting surface. However, mounting surface 12 can be of any shape and surface configuration. Block 14 is fused to cellulosic sheet 16 in a manner as will be described hereinafter.

In the preferred embodiment, the applicator further comprises a handle 18. Handle 18 is of a suitable length for use in pesticide application and, in this embodiment, is formed to be detachable from body 10. To provide detachable mounting to body 10, handle 18 is hollowed at, at least, its end 20 to engage telescopically a protrusion 22 on body 10. Handle 18 may be mounted onto body 10 in various other ways, such as, for example, by threaded attachment or snapping engagement without departing from the scope of the present invention.

The applicator of the present embodiment additionally preferably comprises a capping means 24 to provide protection for block 14 when the applicator is not in use. Capping means 24 is attached removably to body 10 by mating threads 26, 28 or other suitable securing means. Modifications can be made in capping means 24 without departing from the scope of the protection of the present invention.

To assemble the pesticide applicator as shown in FIG. 1B, a novel method of wax to surface attachment is employed using an intermediate layer of cellulosic material and microcrystalline wax. Cellulosic material 16 is first mounted to mounting surface 12 by means of suitable adhesives. The solid carrier containing microcrystalline wax is heated to a suitable temperature to render the carrier molten. The molten carrier must additionally have a sufficient level of heat energy, such that when the cellulosic material is brought into contact with the molten carrier, heat energy is transferred to the cellulose and the temperature of the cellulose is quickly raised to a value above the melting point of the carrier. In this way, the molten carrier is able to infiltrate the cellulose and surround the fibres of the cellulosic material. Thus, when the carrier is allowed to cool, a bond is formed between the cellulose and the carrier that will be as strong as the carrier itself. The microcrystalline wax, then acts as an adhesive in the binding of the carrier to the cellulose.

The temperature of the molten carrier must be raised to a level that will allow infiltration of the carrier into the cellulosic material, and it must be understood that the temperature must be sufficiently high to prevent any spontaneous solidification of the carrier when it is brought into contact with the cellulosic material. Thus, in the preferred embodiment, the temperature of the molten material is brought to at least 100° C. At this temperature, when the cellulosic material is brought into contact with the carrier, the residual water present in the cellulosic material will be raised to the boiling point. Thus, as the cellulose cools a vacuum will be formed which draws the wax into the cellulose. In the preferred embodiment, the molten carrier will be cooled in a mould to cause the carrier to solidify in a predetermined shape, so as to have a carrier block which fits within capping means 24.

While, in the preferred embodiment, the attachment of the cellulosic material to the mounting surface is completed prior to contact with the carrier, this is not necessary in all embodiments.

Figure 2:
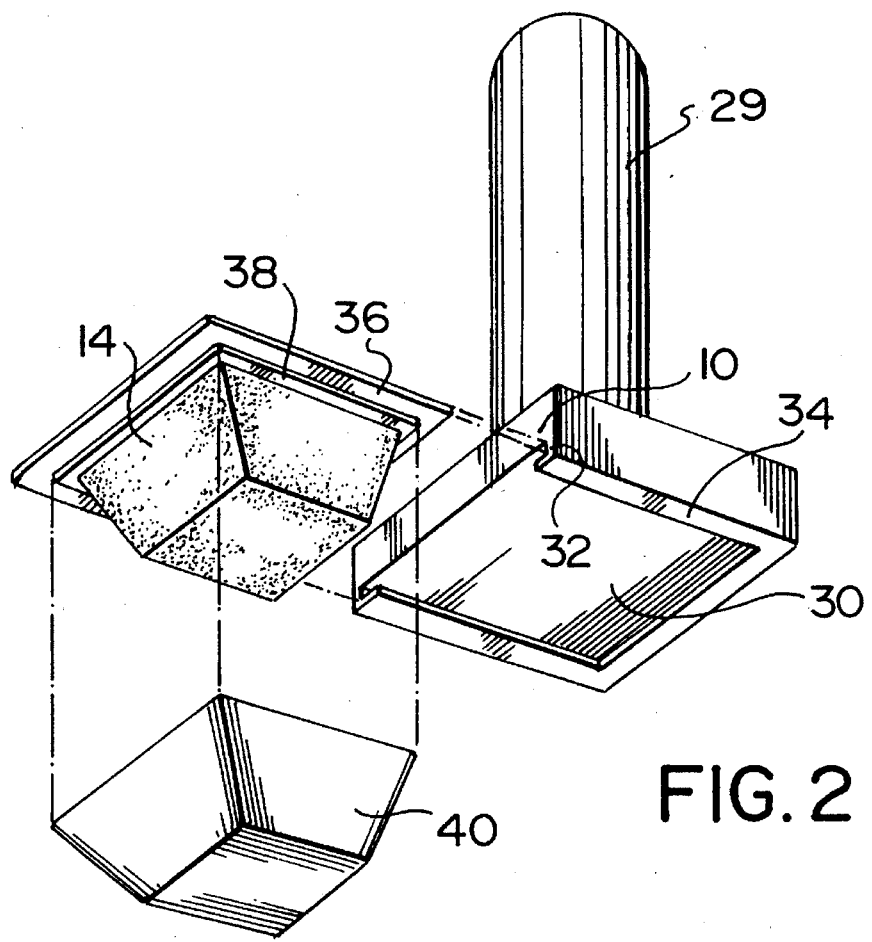
FIG. 2 is a perspective view of an alternative applicator of the present invention.

Referring to FIG. 2, there is shown an alternate preferred embodiment of an applicator of the present invention. The applicator of the alternate preferred embodiment comprises a body 10 having an integral handle 29 and a mounting surface 30. Mounting surface 30 preferably comprises a continuous flange 32 extending about three sides of the periphery of surface 30. Flange 32 comprises a return 34 substantially parallel to mounting surface 30. In this way, the mounting surface is provided with a slot to accept and engage a card 36, which in turn supports a block of pesticide-containing solid carrier 14. In this preferred embodiment, card 36 is formed from cellulosic material, such as wood or card board and block 14 is fused directly to card 36 by means of the novel carrier to surface attachment method. Alternatively, card 36 can be formed of other materials such as metals or plastics. When card 36 is formed of such materials, the carrier block is attached to the card by means of an intermediate layer of the cellulosic material as is described with respect to the embodiment of FIGS. 1A and 1B.

In the alternate preferred embodiment, card 36 is further formed with a central raised portion 38. Block 14 is fused to this raised portion. Thus, when card 36 is inserted into mounting surface 30, raised portion 38 will be substantially flush with, or extend beyond, the return 34. In this way all of block 14 is outside return 34 and therefore block 14 is fully accessible for use. In addition, capping means 40 is provided which fits over and engages raised portion 38 and provides protection for block 14, both during transport of the card/block arrangement and when the card is mounted on the applicator.

The embodiment of FIG. 2 provides a reusable applicator body which can be reloaded with pesticide blocks. This is accomplished simply by sliding out the card 36 with the old pesticide block and sliding in a new card 36 with a fresh block.

Applicators, mentioned above, can be formed of any suitable materials such as plastic or metals. Alternatively, the applicator of the present invention may be formed entirely of a cellulosic material such as wood or cardboard. Such an applicator allows the direct mounting of the carrier block onto the mounting surface of the applicator.

The solid pesticide composition of the present invention comprises a pesticide, a solid carrier and a sufficient quantity of a plant product which is able to absorb liquid to form a gel. The plant product acts to allow the dispersion of the pesticide into the wax and maintains the pesticide in suspension in the wax. Starch or flour derived from plant products are preferred. Pesticides useful in the present composition are any of insecticides, bactericides, herbicides or a combination of any of the foregoing. For example, CONFRONT™, a water soluble amine available from Dow Chemical Co. can be used in a herbicide composition of the present invention. The pesticide is present in the composition in an amount which will vary depending on the specific activity of the pesticide employed.

The solid carrier is solid at ambient temperatures, having a melting point of at least 35° C. Suitable solid carriers are solid soaps, beeswax and mixtures of, by weight, 1–40% paraffin oil and 60–99% paraffin wax; 1–30% microcrystalline wax, 5–40% paraffin oil, and 60–95% paraffin wax. Preferably, the solid carrier comprises at least some microcrystalline wax. The presence of such wax increases the melting point of the carrier and increases the adhesive properties of the wax. Thus, preferably the solid carrier comprises 10% microcrystalline wax, 15% paraffin oil and 75% paraffin wax.

The flour or starch acts to promote the association of the pesticide with the wax and to maintain the pesticide in suspension in the wax. Flour derived from plant products is preferred for use in the solid pesticide composition and more preferably, grain flour such as wheat flour is used.

To produce the solid pesticide composition, the solid carrier is first heated to a temperature above its melting point without increasing the temperature beyond that of the boiling point of the pesticide to be added.

While the molten carrier is agitated, as by stirring, the desired amount of flour is added which becomes dispersed in the wax. Agitation is maintained while the desired amount of liquid pesticide is added. Immediately upon addition of the liquid, the starch and pesticide combine to form a viscous gel which remains suspended in the wax. The composition is allowed to cool. In this way, the pesticide is dispersed through the solidified carrier substantially without stratification.

Preferably, the flour is used in an amount sufficient to allow the dispersion of the pesticide within the carrier. Preferably, flour in an amount of 5–50% by weight of the pesticide composition is employed. The amount of flour used in the composition can depend on the amount of pesticide required to be added to the composition for the final pesticide composition to exhibit effective pesticidal activity.

Preferably, however, a uniform amount of flour is added to the carrier to avoid experimentation to determine the preferred amount of flour to be added for each amount of pesticide used. Thus, most preferably the flour is added to the solid carrier in amount of about 15–20% by weight.

The following examples show non-limitative formulations, by weight, of pesticidal compositions according to the present invention and can be used with the presently described inventive pesticide applicator.

| EXAMPLE 1 | |
|---|---|
| Microcrystalline wax | 13.2% |
| Paraffin wax | 52.8% |
| Paraffin oil | 11.0% |
| Flour | 17.0% |
| CONFRONT | 6.0% |
| EXAMPLE 2 | |
| Microcrystalline wax | 12.5% |
| Paraffin wax | 50.0% |
| Paraffin oil | 7.3% |
| Flour | 17.0% |
| TURFLON II ™* | 13.2% |

*TURFLON II is available from DOW Chemicals Co.

The Embodiments of the Invention in which an Exclusive Property or Privilege is claimed are defined as follows:

1. A pesticide applicator comprising a mounting surface, a block of pesticide-containing solid carrier and an intermediate layer of cellulosic material for mounting the pesticide-containing solid carrier onto the mounting surface, wherein the block of pesticide-containing solid carrier contains microcrystalline wax.

2. The pesticide applicator of claim 1 further comprising an elongated handle formed integral with the mounting surface.

3. The pesticide applicator of claim 1 further comprising an elongated handle for attachment to a portion of the mounting surface.

4. The pesticide applicator of claim 1 wherein said layer of cellulosic material comprises a sheet of paper or wood, attached by means of adhesives to the mounting surface and fused to the pesticide-containing solid carrier.

5. The pesticide applicator of claim 1 wherein said layer of cellulosic material comprises a sheet of paper or wood, attached by means of mechanical attachments to the mounting surface and fused to the pesticide-containing solid carrier.

6. The pesticide applicator of claim 1 further comprising a capping means, formed to extend removably over the block of pesticide-containing solid carrier and engage with a portion of the applicator.

7. The pesticide applicator of claim 1 wherein the pesticide-containing solid carrier further comprises a plant product which is able to absorb liquid to form a gel.

8. A pesticide applicator comprising a mounting surface and a block of pesticide-containing solid carrier, wherein the applicator mounting surface is formed from cellulosic material and the pesticide-containing solid carrier contains microcrystalline wax and is fused directly to the mounting surface.

* * * * *